United States Patent [19]
Henkes, Jr.

[11] 3,963,933
[45] June 15, 1976

[54] MAMMOGRAPHY FIXTURE
[75] Inventor: John L. Henkes, Jr., Latham, N.Y.
[73] Assignee: General Electric Company, Schenectady, N.Y.
[22] Filed: Aug. 18, 1975
[21] Appl. No.: 605,418

[52] U.S. Cl. .................................. 250/456; 250/451
[51] Int. Cl.² ........................................ G03B 41/16
[58] Field of Search ............ 250/451, 456, 439, 360

[56] References Cited
UNITED STATES PATENTS

| | | | |
|---|---|---|---|
| 3,578,971 | 5/1971 | Lasky | 250/456 X |
| 3,867,634 | 2/1975 | Hounsfield | 250/456 X |
| 3,881,110 | 4/1975 | Hounsfield et al. | 250/456 X |

*Primary Examiner*—Davis L. Willis
*Attorney, Agent, or Firm*—Jack E. Haken; Joseph T. Cohen; Jerome C. Squillaro

[57] ABSTRACT

A fixture for shaping and compressing a pendant breast during tomographic mammography procedures. The breast extends pendantly downward into a fluid transmission medium having x-ray absorption characteristics substantially equal to those of human tissue. The breast is upwardly compressed and shaped into a cylindrical form by a thin membrane containing a body of pressurized water and affixed to an upwardly directed concave pan. Tomographic scans are accomplished by rotating an x-ray source and detector about a vertical axis passing through the breast and translating the source and detector vertically along the axis.

11 Claims, 2 Drawing Figures

MAMMOGRAPHY FIXTURE

BACKGROUND OF THE INVENTION

This invention concerns devices for positioning body organs during x-ray examination. More specifically, this invention concerns fixtures for axially compressing a pendant breast during tomographic mammography procedures.

Cancer of the breast is a leading killer of American women. Experience indicates that this desease is most readily treated following early detection of malignent tumors. A major effort is, therefore, under way to provide large scale screening for symptoms of this condition among the female population.

Experience has shown that metastatis generally occurs in breast tumors between 1 and 3 centimeters in diameter. The x-ray density resolution of mammograms (photographic x-rays of the breast) is generally inadequate to distinguish breast tumors of less than 3 centimeters in diameter. Recently developed x-ray tomographic techniques allow electronic imaging of internal tissue density distributions with far greater resolution than is possible with photographic techniques. These techniques are described, for example, in U.S. Pat. Nos. 3,778,614 to Hounsfield and 3,881,110 to Hounsfield et al. A copending U.S. Pat. application, Ser. No. (RD-8312) by R. Redington and J. Henkes (which is assigned to the assignee of this patent application) describes the use of tomographic x-ray techniques for the detection of tumors in pendant breasts and is hereby incorporated by reference in this disclosure.

In accordance with the above referenced copending United States patent application, the detection of tumors in the periphery of the breast may be enhanced by immersing the breast in a fluid medium having x-ray transmission characteristics which are substantially equal to those of soft human tissue. A mixture of water with surfactants and antifoaming agents has been found to be ideally suited for this purpose.

Tomographic x-ray techniques reconstruct sectional images of body tissue from multiple measurements of x-ray transmission characteristics along a plurality of paths through a plane in the tissue. A relatively large number of x-ray exposures, as compared to photographic techniques, are necessary for the development of tomographic image of the breast. Patient's safety dictates that the number of x-ray images, and therefore the total radiation exposure, be minimized during these procedures.

SUMMARY OF THE INVENTION

In accordance with the present invention, we provide a fixture for compressing a pendant breast during tomographic mammagraphy procedures. The breast is tomographically scanned by an x-ray source and detector rotating about a vertical axis passing through the breast. Sectional views through successive planes of the breast are generated by translating the source and detector along the vertical axis. A fluid transmission medium surrounds the breast to provide high resolution in the peripheral tissue. The nipple and breast are compressed upward by a body of pressurized water contained behind a thin membrane. The number of sectional views required to image the compressed breast is necessarily smaller than those of the extended pendant breast and number of calculations necessary to image the breast and the total radiation dose to the patient are therefore reduced.

It is, therefore, an object of this invention to provide fixtures for compressing pendant breasts during tomographic mammography procedures.

It is another object of this invention to provide fixtures for reducing the calculation time required to tomographically image a breast.

Another object of this invention is to reduce the radiation dosage to patients undergoing tomographic mammography procedures.

BRIEF DESCRIPTION OF THE DRAWINGS

The novel features believed characteristic of the present invention are set forth in the appended claims. The invention itself, together with further objects and advantages thereof, may best be understood with reference to the following detail description, taken in connection with the appended drawings in which:

DESCRIPTION OF THE PREFERRED EMBODIMENT

The above-referenced, copending patent application of R. Redington and J. Henkes describes a tomographic mamography system for determining tissue densities in a succession of parallel planes passing horizontally through a pendant breast. An x-ray source and detector are disposed on opposite sides of the breast and revolve about a vertical axis passing through the breast. A succession of x-ray exposures are made during the revolution to determine the x-ray transmission characteristics along successive paths through the breast tissue. Transmission information from the x-ray detector is then processed in a digital computer which reconstructs a sectional image of tissue densities in the plane. The x-ray source and detector translate along the vertical axis after each revolution to produce a series of sectional images which may be combined to depict three-dimensional characteristics of the tissue. The minimum tumor size which may be resolved by the examination procedure is a function of the spacing between adjacent scan planes. Present detection standards indicate that a spacing of not more than 1 centimeter between adjacent scan planes is suitable for the effective, early diagnosis of malignant breast tumors.

The reconstruction of a single tomographic image requires over one hundred x-ray exposures and the solution of thousands of simultaneous equations in the digital computer. The net radiation dose received by the patient and the total computer time required for image reconstruction are necessarily proportional of the number of planes scanned during the mamography procedure. It is, therefore, highly desirable to reduce the number of tomographic scans required to produce accurate, reliable information during such procedures.

A normally pendant breast assumes a substantially conical shape so that successively scan horizontal planes will, necessarily, include tissue sections of decreasing area. The nature of the tomographic reconstruction process is such, however, that the radiation dose and computation time remains constant regardless of the tissue areas scanned in a plane. Processing time and patient radiation exposure may, therefore, be substantially reduced if the volume of the breast is compressed from a substantially conical structure into a substantially cylindrical form.

A high probability of error exists in tomographic measurements for image elements which include high x-ray absorption density gradients. Such gradients occur, for example, at an air tissue interface and present serious limitations in resolving breast tumors within approximately 1 centimeter of the skin. These measurement errors may, however, be substantially eliminated by immersing the breast in a medium having x-ray transmission characteristics substantially equal to those of human tissue, for example, water. The above-referenced patent application describes structures for supporting a female patient with a breast pendantly extending into a water-filled container.

Figure 1:
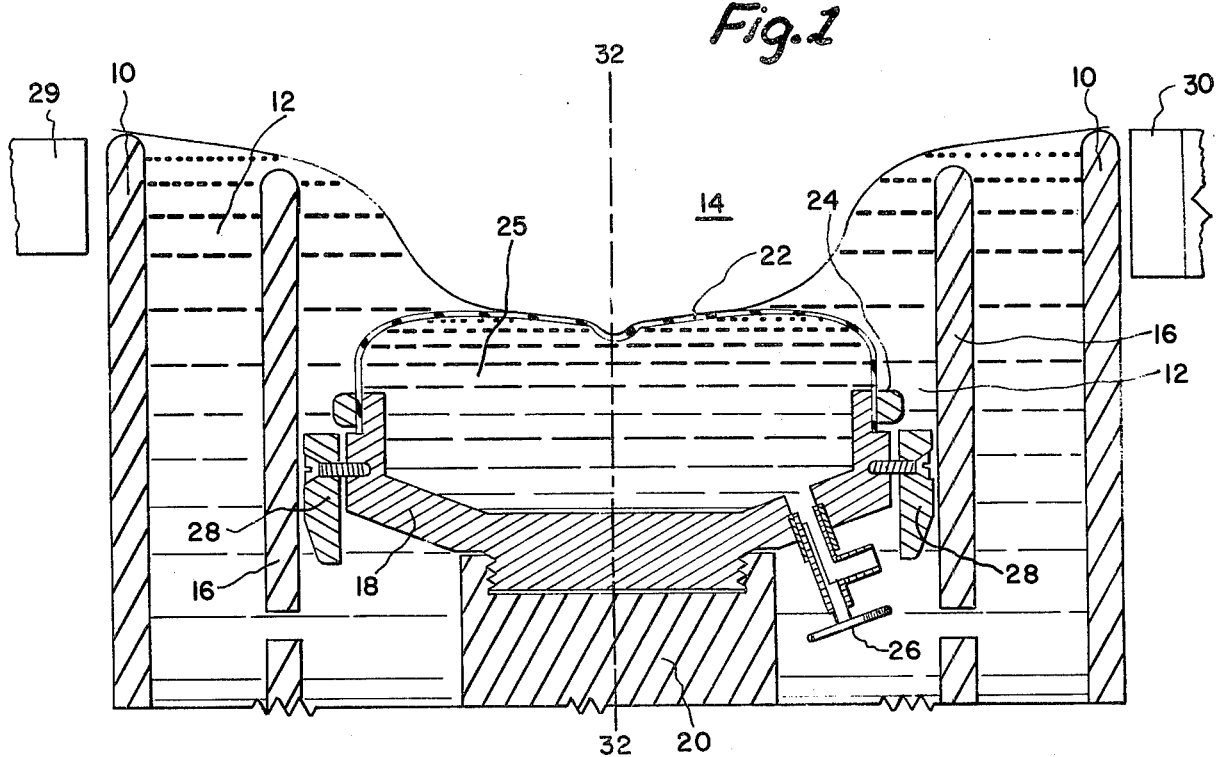
FIG. 1 is a side sectional view of a breast compressing fixture in accordance with the present invention.
Figure 2:
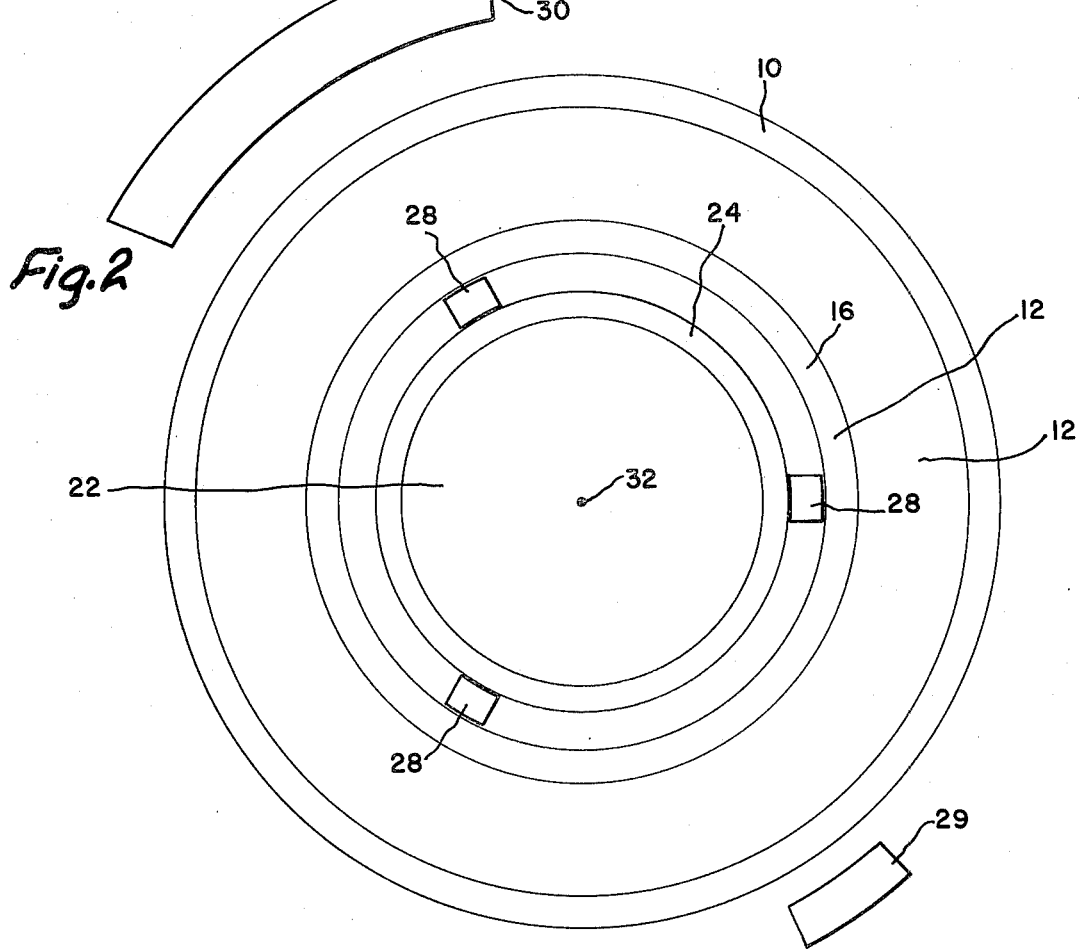
FIG. 2 is a top view of the fixture of FIG. 1.

FIGS. 1 and 2 are views of a fixture for compressing and shaping a pendant breast during tomographic mammography procedures. A cylindrical water container 10 is filled with a fluid x-ray transmission medium 12 which may, for example, comprise water which has been out-gased and treated with a combination of surfactants, antifoaming, and algicidal agents. A patient lies in prone position above the container 10 on a table (not shown) with a breast 14 extending pendantly into the transmission medium 12. A cylindrical baffle 16 surrounds the breast to prevent motion which might otherwise be caused by fluid currents flowing within the transmission medium 12. A concave pan 18 is suspended beneath the breast on an adjustable support fixture 20. The concavity of the pan 18 is upwardly disposed and is covered with a thin membrane 22 which is clamped and sealed around the edge of the pan 18 with a collar 24. The volume between the membrane 22 and the pan 18 is filled with a fluid x-ray transmission medium 25 which may be identical to the medium 12. The transmission medium 25 is inserted into the pan 18 through a valve 26 under slight pressure which upwardly expands the membrane 22. The filling procedure may be conducted with the valve 26 uppermost to allow the escape of trapped air bubbles which might otherwise become lodged beneath the diaphragm 22.

The height of the membrane 22 is adjusted by means of threads on the support fixture 20 to effectively compress the breast into a substantially cylindrical form and thus minimize the x-ray exposure and computation time necessary to depict its tissue structure. The height of the membrane must be sufficient to effectively compress the breast but not so high as to exclude the uppermost tissues from the scan area. I have determined that a spacing of approximately 6 cm between the uppermost extension of the membrane and the top of the scan area is optimum for large samples of patients examined. The membrane 22, pan 18, and fixture 20 are separated from and centered within the baffle 16 by radial spacers 28 positioned around the circumference of the pan 18.

The membrane 22 may be formed from any thin, relatively elastic material having an x-ray absorption characteristic which is near that of human tissue. We have found, however, that a flat topped, convex diaphragm of a relatively stiff plastic, for example, Lexan polycarbonate having a thickness between approximately 0.1 mm and approximately 0.8 mm provides an effective compression and cylindrical shaping of the breast without discomfort to the patient. Alternately, the membrane 22 may be constructed from surgical latex having a thickness between approximately 0.1 mm and approximately 0.8 mm. Latex, however, is relatively flexible and assumes a spherical form under the influence of pressure in the transmission medium 25, and is, therefore, somewhat less effective than plastic in shaping the breast. The membrane should in all cases be sufficiently thin as to be invisible during the scan procedure and to exert a negligible influence on the image reconstruction calculations.

Successive tomographic scans of the breast 14 tissue are conductd by revolving an x-ray source 29 and an x-ray detector 30 about an axis 32 which extends vertically through the breast 14, the membrane 22, and the pan 18. Successive planes in the breast are scanned by translating the detector 30 and the x-ray source 28 vertically along the axis 32 after each revolution.

The fixture of the present invention allows effective cylindrical shaping and compression of a vertically pendant breast during tomographic, x-ray mammography procedures. Cylindrical compression produced by the fixture allows accurate and effective detection of breast tumors with minimum radiation dosage and processing time. The breast is compressed by a pressurized transmission medium contained below a thin membrane which, by eliminating high gradients in x-ray absorption density, minimizes computational errors at the periphery of the breast.

While the invention has been described in detail herein in accord with certain preferred embodiments thereof, many modifications and changes therein may be effected by those skilled in the art. Accordingly, it is intended by the appended claims to cover all such modifications and changes as fall within the true spirit and scope of the invention.

The invention claimed is:

1. A fixture for compressing a pendant breast during tomographic mammography procedures comprising:
   a substantially circular pan having an upwardly directed concave surface;
   a thin, elastic membrane disposed over said concave surface and sealably affixed to the circumference of said pan; and
   a first fluid transmission medium disposed between said pan and said membrane whereby a pendant breast compressed against said membrane is conformally pressed into a substantially cylindrical form.

2. The fixture of claim 1 wherein said first fluid comprises materials having x-ray absorption densities substantially equal to those of soft human tissue.

3. The fixture of claim 2 wherein said first fluid comprises water.

4. The fixture of claim 2 wherein said membrane extends convexly upward from said pan.

5. The fixture of claim 4 wherein the central, upper surface of said membrane is substantially flat.

6. The fixture of claim 4 wherein said membrane comprises polycarbonate plastic having a thickness between approximately 0.1 mm and approximately 0.8 mm.

7. The fixture of claim 4 wherein said membrane comprises latex.

8. The fixture of claim 4 further comprising:
   means for vertically adjusting the position of said pan.

9. The fixture of claim 8 further comprising:
   a substantially cylindrical container symmetrically disposed around said pan and said membrane and about a vertical axis oriented through said breast; and a second fluid transmission medium disposed within said container and around said pan and said membrane, said second fluid transmission medium having an x-ray absorption characteristic substantially equal to that of soft human tissue.

10. The fixture of claim 9 further comprising:

an x-ray source disposed outside and adjacent a vertical wall of said cylindrical container; and an x-ray detector disposed outside and adjacent a vertical wall of said cylindrical container and opposite said x-ray source, said x-ray source and said x-ray detector being further disposed in a common horizontal plane.

11. The fixture of claim 10 further comprising:

means for revolving said x-ray source and said x-ray detector symmetrically about a vertical axis passing through said breast, said membrane, and said cylindrical container and aligned coaxially therewith; and means for translating said x-ray source and said x-ray detector along said axis.

* * * * *